United States Patent

Metzner et al.

Patent Number: 5,964,138
Date of Patent: *Oct. 12, 1999

[54] CLAMPING DEVICE FOR A BLADE-SHAPED CUTTING KNIFE OF A MICROTOME

[75] Inventors: Rolf Metzner, Dossenheim; Manfred Biehl, Meckesheim, both of Germany

[73] Assignee: Leica Instruments GmbH, Wetzlar, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/534,540

[22] Filed: Sep. 27, 1995

[30] Foreign Application Priority Data

Sep. 30, 1994 [DE] Germany ............... 44 35 072

[51] Int. Cl.⁶ ................................... B26D 7/26
[52] U.S. Cl. ................. 83/699.51; 83/856; 83/915.5
[58] Field of Search ................ 83/915.5, 170, 83/171, 699.51, 699.61, 856, 698.71

[56] References Cited

U.S. PATENT DOCUMENTS

| | | | |
|---|---|---|---|
| 2,439,671 | 4/1948 | Ott | 83/915.5 X |
| 3,308,704 | 3/1967 | Burkhardt | 83/915.5 X |
| 3,527,133 | 9/1970 | Lankes et al. | 83/699.51 |
| 3,733,948 | 5/1973 | Pickett | 83/915.5 X |
| 3,866,642 | 2/1975 | Walser | 83/170 X |
| 4,014,232 | 3/1977 | Mauger | 83/698.71 X |
| 4,252,163 | 2/1981 | Onda et al. | 83/699.51 X |
| 4,472,989 | 9/1984 | Endo | 83/915.5 X |
| 4,611,484 | 9/1986 | MacKissinger, Jr. et al. | 83/698.71 X |
| 4,690,023 | 9/1987 | Berleth et al. | 83/915.5 X |
| 4,700,600 | 10/1987 | Pickett | 83/915.5 X |
| 5,099,735 | 3/1992 | Kempe et al. | 83/700 |
| 5,148,729 | 9/1992 | Krumdieck | 83/915.5 X |
| 5,211,097 | 5/1993 | Grasselli | 83/856 X |
| 5,522,294 | 6/1996 | Krumdieck | 83/915.5 X |

FOREIGN PATENT DOCUMENTS

| | | | |
|---|---|---|---|
| 2185 | 9/1900 | Germany | 83/699.51 |
| 1191130 | 4/1965 | Germany | 83/915.5 |
| 2143529 | 3/1973 | Germany | 83/915.5 |
| 34 13 250 | 2/1985 | Germany . | |
| 36 16 659 | 8/1987 | Germany . | |
| 89 10 373 U | 11/1989 | Germany . | |
| 89 14 782 U | 3/1990 | Germany . | |
| 2182881 | 5/1987 | United Kingdom | 83/915.5 |

*Primary Examiner*—Rinaldi I. Rada
*Assistant Examiner*—Charles Goodman
*Attorney, Agent, or Firm*—Foley & Lardner

[57] ABSTRACT

A clamping device for a blade-shaped cutting knife of a microtome. The clamping device comprises a base part having a recess, a knife receptacle, an eccentric rod, and setscrews. The knife receptacle includes a blade rest and a pressure plate which is received in the recess of the base part. The eccentric rod is rotatably mounted in the base part and is provided for clamping the cutting knife between the pressure plate of the knife receptacle and the blade rest. The setscrews allow for both lateral and vertical movement of the pressure plate. Thus, by adjusting the setscrews, the edge of the pressure plate may be aligned with the cutting edge of the knife and variation in the thickness or geometry of cutting knife blade may be accommodated.

8 Claims, 1 Drawing Sheet

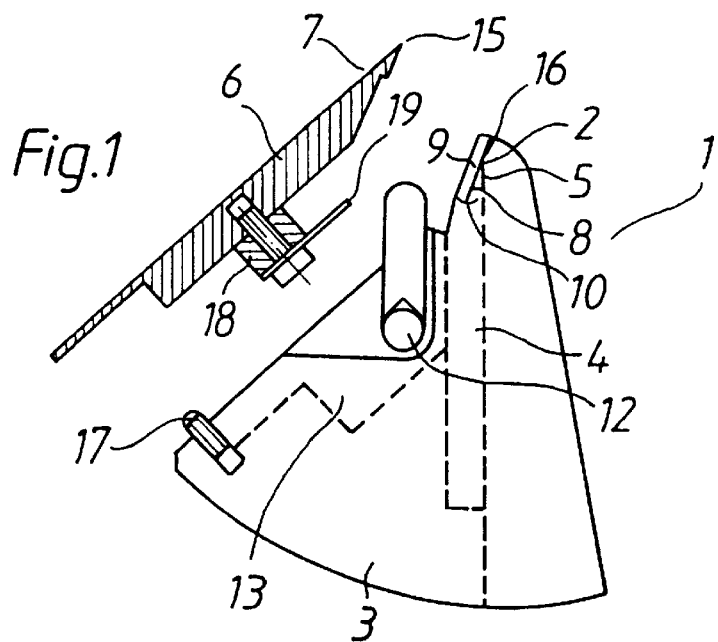
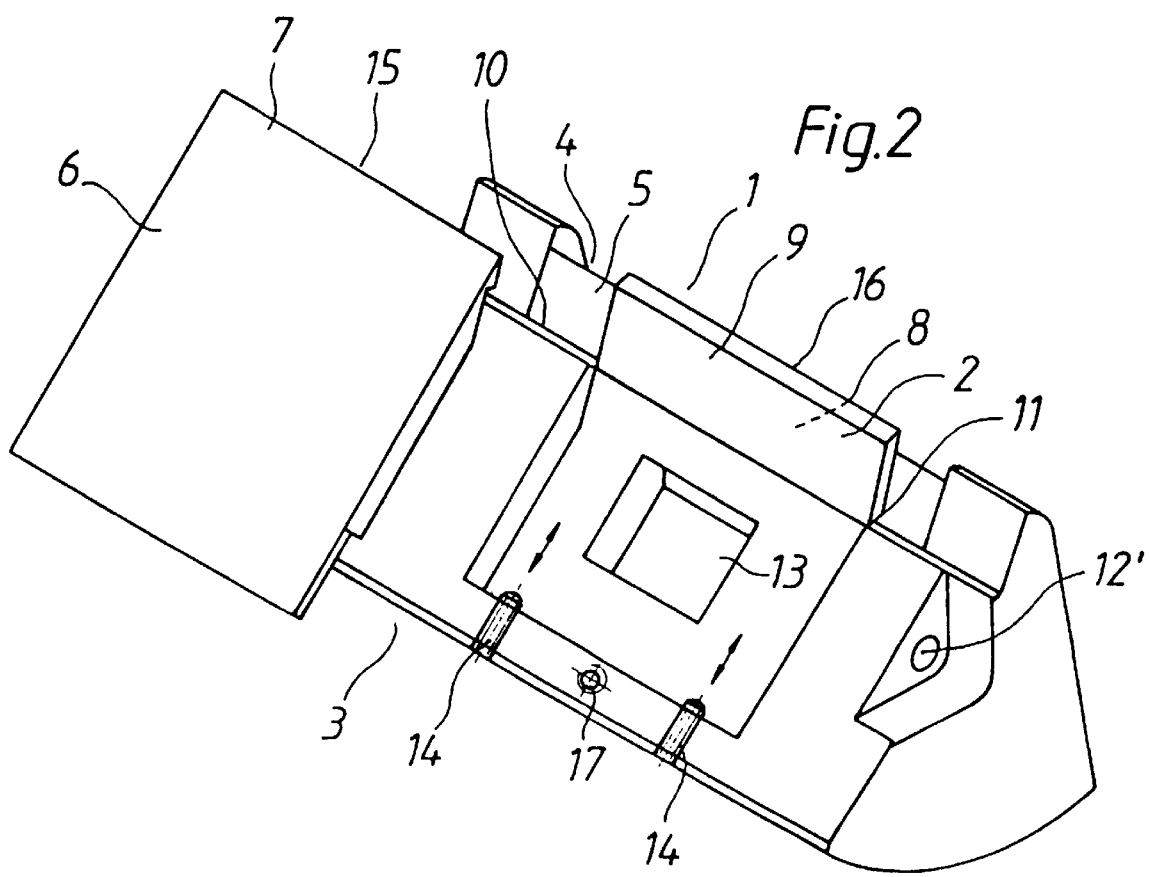

CLAMPING DEVICE FOR A BLADE-SHAPED CUTTING KNIFE OF A MICROTOME

BACKGROUND OF THE INVENTION

1. Field of the Invention

The invention relates to a clamping device for a blade-shaped cutting knife of a microtome.

2. Description of Related Art

Clamping device are used in microtomes, particularly in rotary microtomes, for receiving thin blade-shaped cutting knives. In microtomy, knives made of hard metal and steel, known as so-called "disposable blades", are generally employed as blade-shaped cutting knives. In order to keep these known blade-shaped cutting knives accurate during the cutting operation, it is beneficial to include specially designed clamping devices which are used on the microtome.

For example, DE 36 16 659 C1 discloses a clamping device for a wedge-shaped cutting knife of a microtome, in which the cutting knife is arranged between a stationary and an adjustable clamping jaw. The adjustable clamping jaw together with the cutting knife can be adjusted via a threaded spindle in the direction of the specimen to be cut.

DE 89 14 782 U1 discloses a clamping device for the wedge-shaped cutting knife of a microtome, in which the spine of the cutting knife bears on a support strip which is adjustable via two setscrews. By means of the adjustable support strip, the knife cutting edge can be aligned with the object to be cut via two screw bolts.

Known clamping devices for blade-shaped cutting knives as disclosed, for example, in DE 34 13 250 and DE 89 10 373 U1 are generally adapted to receive diverse cutting-knife geometries. The knife receptacle may be formed of a wedge-shaped base part, a clamping jaw arranged above the base, and an abutment device. The clamping jaw is connected to the base part via screws such that it is possible to accommodate cutting knives having various thicknesses in the knife receptacle.

However, the above-referenced clamping devices involve very high costs associated with their manufacture. Further, because the front edge of the clamping jaw is in parallel alignment with the knife cutting edge, precise positioning of the cutting knife is difficult to attain.

SUMMARY OF THE INVENTION

It is therefore an object of the present invention to provide a clamping device for a cutting knife of a microtome which can be manufactured at reduced costs. It is a further object to provide a clamping device which permits precise alignment of the clamping jaw with the knife cutting edge in a simple manner.

In accordance with these objectives, the present invention provides a clamping device for a blade-shaped cutting knife of a microtome. The clamping device comprises a base part having a recess, a knife receptacle, an eccentric rod, and setscrews. The knife receptacle includes a blade rest and a pressure plate which is received in the recess of the base part. The eccentric rod is rotatably mounted in the base part and is provided for clamping the cutting knife between the pressure plate of the knife receptacle and the blade rest. The setscrews permit both lateral and vertical movement of the pressure plate. Thus, by adjusting the setscrews, the edge of the pressure plate may be aligned with the cutting edge of the knife and variation in the thickness or geometry of the blade of the cutting knife may be accommodated.

Further objects, features, and advantages of the invention will become apparent from the figures and detailed description which follow.

BRIEF DESCRIPTION OF THE DRAWINGS

FIG. 1 shows a partial sectional view of the clamping device according to the present invention.

FIG. 2 shows a perspective view of the clamping device according to the present invention.

DETAILED DESCRIPTION OF THE PREFERRED EMBODIMENTS

FIG. 1 shows a section through the clamping device 1 which includes a base part 3. The clamping device 1 further includes a knife receptacle 4 including a blade rest 5 and a pressure plate 6 for receiving and accomodating the cutting knife 2. The cutting knife 2 bears with its spine surface 8 on the blade rest 5 and with its front surface 9 on the clamping jaw 7 of the pressure plate 6. The blade rest 5 has a recess 10, on which the narrow spine surface 11 of the cutting knife 2 which is located opposite the knife cutting edge 16 is supported. A terminal edge of the spine surface 8 forms the cutting edge 16. A rotatably mounted, chamfered eccentric rod 12 is provided in the base part 3 for clamping the cutting knife 2 between the clamping jaw and the blade rest 5.

The base part 3 has a recess 13 which is designed for receiving the pressure plate 6. The pressure plate 6 has provided thereon a screwed-on spacer piece 18 with a clamping plate 19 which cooperates with the eccentric rod 12 to provide clamping of the cutting knife 2.

To adapt the knife receptacle 4 to different cutting-knife thicknesses and geometries, a setscrew 17 with a spherical head, on which the pressure plate 6 is supported, is arranged in the base part 3. A gap is provided for the cutting knife 2 in the knife receptacle 4. The gap can be specifically set by screwing the setscrew into or out of the base part 3, which adjusts the position of the pressure plate 6 with respect to the base part 3.

For clamping the cutting knife 2, first the eccentric rod 12 is drawn out of the guide 12' in the base part 3. The now free recess 13 receives the spacer piece 18, and the clamping plate 19 which are attached to the pressure plate 6. The eccentric rod 12 can subsequently be pushed into the associated guide 12'. Thus, the eccentric rod 12 is guided between the clamping plate 19 and the pressure plate 6, so that clamping takes place as a result of the rotation of the eccentric rod 12.

During this clamping, the clamping jaw 7 of the pressure plate 6 is not pressed against the front surface 9 of the cutting knife 3 by means of a forwardly directed tilting movement, but the entire pressure plate 6 is drawn linearly towards the base part 3. This movement of the pressure plate 6 is limited by the thickness of the cutting knife 2 and by the position of the setscrew 17.

FIG. 2 shows a view of the clamping device 1 together with the base part 3, the pressure plate 6 and the eccentric-rod guide 12'. At least one and preferably two setscrews 14 are arranged parallel and next to one another in the base part 3. By screwing these setscrews 14 into or out of the base part 3, the relative position of the pressure plate 6 is adjusted, thus allowing the front edge 15 of the clamping jaw 7 to be aligned parallel to the knife cutting edge 16. Production-related tolerances or different cutting-knife geometries can thereby be compensated in a simple way. Only when the clamping jaw 7 is positioned in absolute parallel orientation relative to the knife cutting edge 16 can a cutting quality be guaranteed.

As shown in the figures, the geometry of the wedge-shaped base part 3 together with the knife receptacle 4 is adapted to the geometry of the pressure plate 6. The pressure plate 6 is parallel to the surface of the base part 3 in all regions. This guarantees that during the clamping of the cutting knife 2, a uniform pressure is exerted over the entire length of the knife blade.

The exemplary embodiment of the clamping device described and represented in the figures is distinguished not only by the simple construction, but also by its ergonomically favorable handling, since the pressure plate can be removed from the base part simply by drawing the eccentric rod out of the guide 12'. The knife receptacle is then readily accessible for changing the cutting knife or for cleaning the receptacle, without the risk of injury.

Additional advantages and modifications will readily occur to those skilled in the art. Therefore, the invention in its broader aspects is not limited to the specific details, and representative embodiments, shown and described herein. Accordingly, various modifications may be made without departing from the spirit or scope of the general inventive concept as defined by the appended claims and their equivalents.

What is claimed is:

1. A clamping device for a blade-shaped cutting knife of a microtome comprising:

a cutting knife having a first spine surface having a terminal edge, a second spine surface, a front surface disposed between the spine surfaces, and a cutting edge which is on said terminal edge of said first spine surface and opposite said second spine surface;

a base part having a recess;

a knife receptacle including a blade rest and a pressure plate with a clamping jaw, said clamping jaw having a front edge and an opposite edge, and said pressure plate being received in said recess of said base part, said cutting knife bearing with said first spine surface on the blade rest and with said front surface on the clamping jaw of the pressure plate, said blade rest having a recess on which the cutting knife bears with said second spine surface;

an eccentric rod rotatably mounted in said base part, said rod being provided for clamping the cutting knife between the clamping jaw of the pressure plate and the blade rest, said pressure plate being releasably fastened to the base part by said eccentric rod, such that the pressure plate is capable of being removed from the base part by movement of the eccentric rod, wherein said pressure plate has provided thereon a spacer piece comprising a clamping plate such that when said clamping device is in an operative position, said eccentric rod being located between a lower surface of the pressure plate and an upper surface of the clamping plate;

at least one first setscrew provided in the recess of the base part, wherein adjustment of said first setscrew permits movement of said pressure plate so as to align said front edge of said clamping jaw with said knife cutting edge;

at least one second setscrew, said second setscrew having a head which supports said opposite edge of said pressure plate, such that adjustment of said second setscrew permits inward or outward adjustment of said pressure plate, thereby allowing for variation in thickness or geometry of said cutting knife.

2. The clamping device as claimed in claim 1, wherein the recess in the base part is provided for receiving the clamping plate.

3. The clamping device as claimed in claim 1, wherein the blade rest is formed as a one-piece element on the base part.

4. The clamping device as claimed in claim 1, wherein the head of the second setscrew is spherical.

5. A clamping device for a blade-shaped cutting knife of a microtome comprising:

a base part having a recess;

a receptacle capable of receiving said cutting knife, said receptacle including a blade rest with a recess and a pressure plate with a clamping jaw, said clamping jaw having a front edge and an opposite edge, and said pressure plate being received in said recess of said base part;

an eccentric rod rotatably mounted in said base part, said rod being capable of clamping said cutting knife between the clamping jaw of the pressure plate and the blade rest, said pressure plate being releasably fastened to the base part by said eccentric rod, such that the pressure plate can be removed from the base part by movement of the eccentric rod, wherein said pressure plate has provided thereon a spacer piece comprising a clamping plate such that when said clamping device is in an operative position, said eccentric rod being located between a lower surface of the pressure plate and an upper surface of the pressure plate;

at least one first setscrew provided in the recess of the base part, wherein adjustment of said first setscrew permits movement of said pressure plate so as to raise or lower said front edge of said clamping jaw;

at least one second setscrew, said second setscrew having a head which supports said opposite edge of said pressure plate, such that adjustment of said second setscrew permits inward or outward adjustment of said pressure plate, thereby allowing for variation in thickness or geometry of said cutting knife.

6. The clamping device as claimed in claim 5, wherein the recess in the base part is provided for receiving the clamping plate.

7. The clamping device as claimed in claim 5, wherein the blade rest is formed as a one-piece element on the base part.

8. The clamping device as claimed in claim 5, wherein the head of the second setscrew is spherical.

* * * * *